United States Patent [19]

Landsiedel et al.

[11] Patent Number: 5,344,482
[45] Date of Patent: * Sep. 6, 1994

[54] USE OF THIADIAZOLES AS BIOCIDES FOR MATERIAL PROTECTION

[75] Inventors: Horst Landsiedel, Unna; Dirk Ventur, Bochum, both of Fed. Rep. of Germany

[73] Assignee: Witco GmbH, Bergkamen, Fed. Rep. of Germany

[ * ] Notice: The portion of the term of this patent subsequent to Jul. 26, 2011 has been disclaimed.

[21] Appl. No.: 122,883

[22] Filed: Sep. 15, 1993

[30] Foreign Application Priority Data

Sep. 16, 1992 [DE] Fed. Rep. of Germany ....... 4230956

[51] Int. Cl.$^5$ ............................................... C09D 5/14
[52] U.S. Cl. .................................. 106/18.33; 252/8.6; 252/8.7; 252/380; 252/384; 424/405; 427/384; 427/394; 427/396; 427/397; 514/363; 514/493; 514/642; 523/122; 548/128
[58] Field of Search ...................... 106/18.33; 514/363, 514/642, 493; 548/128; 424/405, 78.09; 427/384, 394, 396, 397; 252/8.6, 8.7, 380, 384; 523/122

[56] References Cited

U.S. PATENT DOCUMENTS

| | | | |
|---|---|---|---|
| 4,209,522 | 6/1980 | Mixan et al. | 106/18.33 |
| 4,711,915 | 12/1987 | Doe, Jr, | 106/18.33 |
| 5,147,443 | 9/1992 | Diehr et al. | 106/18.33 |

FOREIGN PATENT DOCUMENTS

| | | | |
|---|---|---|---|
| 588046 | 12/1959 | Canada | 106/18.33 |
| 2142913 | 8/1971 | Fed. Rep. of Germany . | |
| 2439619 | 2/1975 | Fed. Rep. of Germany | 106/18.33 |
| 38-020133 | 10/1963 | Japan | 106/18.33 |
| 51-009705 | 1/1976 | Japan | 106/18.33 |
| 2173165 | 7/1990 | Japan | 106/18.33 |
| 1356391 | 6/1974 | United Kingdom . | |

OTHER PUBLICATIONS

Green, T. W., *Protective Groups in Organic Synthesis,* John Wiley & Sons, Inc., New York, pp. 288–334 (1981).

*Primary Examiner*—Anthony Green
*Attorney, Agent, or Firm*—Scully, Scott, Murphy & Presser

[57] ABSTRACT

The present invention relates to the use of thiadiazoles of the type

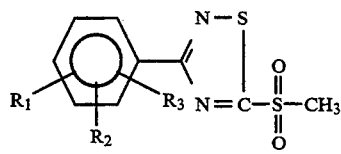

in which $R_1$, $R_2$ and $R_3$ =
  hydrogen,
  alkyl groups having 1–4 carbon atoms
  substituted alkyl groups having 1–4 carbon atoms which are substituted by halogen, carboxyl, hydroxyl or nitro group,
  an alkoxy
  CN, halogen, $NO_2$ or
  COOR in which R=H or alkyl groups 1–4 carbon atoms, and the use of synergistic combinations of thiadiazoles with other biocidal substances as biocides for material protection. The compounds according to-the invention, which are distinguished by a broad, biocidal action spectrum, can be used in particular for wood preservation for preventing the destruction of wood by fungi or bacteria, for the biocidal treatment of plastics and as preservatives or disinfectants. The recommended concentrations for use are 0.01 to 15 percent by weight-preferably 0.1–3.0 percent by weight.

40 Claims, No Drawings

USE OF THIADIAZOLES AS BIOCIDES FOR MATERIAL PROTECTION

The invention relates to thiadiazole compounds and combinations of thiadiazole compounds with other cobiocides which, owing to their bactericidal and fungicidal properties and, especially in the case of the combination products, owing to synergistic biocidal effects, are suitable as disinfectants, wood preservatives and for the bactericidal and fungicidal treatment of paints, textiles, plastics and building materials.

The preparation of novel diazole compounds and their use in pesticidal preparations and for controlling nematodes and plant-damaging fungi is described in DE-A-2 142 913, the contents of which are incorporated by reference.

It has now been found, surprisingly, that the following thiadiazole compounds are effective as a protectant for materials:

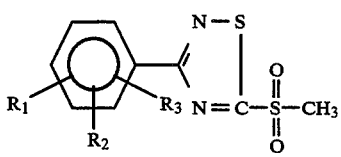

Formula 6 in which

R$_1$, R$_2$ and R$_3$ are independently
hydrogen,
alkyl groups having 1–4 carbon atoms,
substituted alkyl groups having 1–4 carbon atoms which are substituted by halogen, carboxyl, hydroxyl or nitro group,
alkoxy group having 1–4 carbon atoms
CN, halogen, NO$_2$ or
COOR in which R is H or an alkyl group having 1–4 carbon atoms.

As defined hereinabove, the term halogen refers to fluoro, bromo, iodo and especially chloro.

Alkoxy is defined herein as an O-alkyl group wherein alkyl contains 1–4 carbon atoms.

Preferred compounds of Formula I are those in which at least one of R$_1$, R$_2$ and R$_3$ is hydrogen. It is also preferred that at least one of R$_1$, R$_2$ or R$_3$ is hydrogen, alkyl which is either substituted or unsubstituted, halo, nitro or cyano. If alkyl is substituted, it is preferred that the substituents are halogen or nitro. It is more preferred that two of R$_1$, R$_2$ and R$_3$ are hydrogen. It is most preferred that R$_1$, R$_2$ and R$_3$ are all hydrogen.

The present invention also relates to the synergistic combinations of the thiadiazole compounds of Formula I defined hereinabove with other cobiocides, such as, for example, trialkyltin compounds, quaternary ammonium compounds, triazoles, and the like. The preferred salts of the quaternary ammonium compounds are the halides, e.g., chlorides or bromides. Examples of other cobiocides include alkyl(C$_{12}$–C$_{18}$) dimethylbenzylammonium halide (e.g., chloride or bromide), didecyldimethylammonium halide (e.g., chloride), alkyl C$_{12}$–C$_{18}$ trimethylammonium halide (e.g., chloride), [1-(4-chlorophenoxy-3,3-dimethyl-1-(1H-1,2,4-triazol-1-yl)-2-butane-2-one], [1-(2-(2,4-dichlorophenyl)-1,3-dioxolan-2-yl)-methyl-1H-1,2,4-triazol], α-(2-(4-chlorophenyl)-ethyl]-α-(1,1-dimethyl) 1H-1,2,4-triazol-1-ethanol, trialkyltin products containing 1–6 carbon atoms, e.g., tributyltin compounds, such as tri-n-butyltinoxide, tri-n-butyltin naphthenate, tri-n-butyltin benzoate, tri-n-butyltin linoleate, and the like. This combination is also effective in retarding and preventing the growth of wood-destroying or wood-discoloring fungi, bacteria, algae, wood root fungi and molds.

The invention accordingly relates to the use of thiadiazole compounds of the general Formula I as an active ingredient in disinfectants, preservatives, especially wood preservatives and for the bactericidal and fungicidal treatment of paints, textiles, plastics and building materials.

The thiadiazoles of the present invention are effective in disinfectants, for example, technical equipment, such as cooling water systems, drill oil containers, mixing containers for paints, and the like.

The invention furthermore relates to wood preservatives which are characterized in that, in addition to liquid or solid carriers, they contain thiadiazole compounds having Formula I, in particular 5-methylsulfonyl-3-phenyl-1,2,4-thiadiazole, as an active ingredient.

The carriers used in the present invention are those that are typically used in biocidal preparations. These are known to one skilled in the art. Many of the carriers are described in DE-OS-2 142 913 and its equivalent, British Patent No. 1,356,391, the contents of which are incorporated by reference. For instance, liquid carriers useful in the present invention include alcohols containing 1–4 carbon atoms, aliphatic hydrocarbons, including those having boiling points in the range of 130°–250° C., aromatic hydrocarbons containing 6–10 ring carbon atoms and up to a total of 14 carbon atoms, ketones containing 1–5 carbon atoms, mineral oil and the like. Examples include ethanol, xylene, toluene, hexane, pentane, petroleum ether, ligroin, acetones, crystal oil 60 and the like.

The carrier may be a solid. Solid carriers with which the compounds may be incorporated include clays, sands, talc, alkyl resin, wax, paraffins, such as those containing 20–34 carbon atoms, hydrocarbon waxes, such as polyethylene wax and the like.

The invention also relates to the use of thiadiazole compounds of Formula I in combination with cobiocides preferably in a weight ratio of 1:10 to 10:1.

The invention also relates to wood preservatives characterized in that, in addition to liquid or solid carriers, contain thiadiazole compounds according to Formula I in combination with cobiocides as active ingredients.

Wood preservatives which contain thiadiazole compounds in synergistic combination with tributyltin compounds, quaternary ammonium compounds or triazoles are particularly advantageous. Examples include those examples mentioned hereinabove, and especially tri-n-butyltin naphthenate, 1-[2-(2,4-dichlorophenyl)-1,3-dioxolan-2-yl]methyl-1H-1,2,4-triazole, α-[2-(4-chlorophenyl)-ethyl]-α-(1,1-dimethyl)-1H-1,2,4-triazole-1-ethanol, alkyldimethylbenzylammonium chloride, and the like.

The agents according to the invention can be used for wood preservation since, in addition to the prevention of the degradation by wood-destroying fungi, protection from wood-discoloring fungi and bacterial attack are also achieved as a result. Bacteria do not cause degradation of the wood but may promote attack by fungi or lead to discoloration of the wood surface. However, use of the thiadiazole compounds of Formula I protect the surface from bacterial attack.

The agents used in the present invention kill various bacterial and fungi. In addition, the agents used in the present invention prevent their growth. Examples of organisms which the compounds of the present invention are effective against include such bacteria as *Bacillus subtillis, Staphylococcus aureus, Proteus vulgaris,* and the like; yeast, such as *Candida albicans,* and the like; fungi, such as *Aspergillus niger, Ppaecilomyces Variot; Chaetomium globosum, Trichoderma Viride, Cladosporum herbarum, Penicillium funicolosum, Aureobasidium pullulans, Gloeophyllum trabeum,* and the like.

The agents in the form of solutions, and optionally, with dyes and auxiliaries, are introduced into the wood by conventional means, such as brushing, injecting, spraying, immersion and the like.

Furthermore, the agents according to the invention can be used for the biocidal treatment of textiles, plastics and building materials, said agents advantageously being used in the form of formulations such as solutions, emulsions or dispersions with or without binders or with solid carriers or diluents and, if necessary, with the addition of wetting agents, adhesives, emulsifiers and dispersants.

The types of formulations that could be used are well known to one skilled in the art. Examples of formulations are described in DE-OS-2 142 913 and British Patent No. 1,356,391, the contents of both of which are incorporated herein by reference.

Examples of binders include alkyld resins, hydrocarbon resins, acryl copolymers, rosin, asphalt, butumen, pitch, tars, phenolic resins, maleic resins, urea resins, polyvinyl alcohols, polyvinyl chlorides, polyvinyl acetates, polyurethanes, and the like.

Wetting agents include soja lecithins, silicon oils, and the like.

Dyes include pigments based on metal oxides or metal salts, soot, organic pigments, like phthalocyanin, ultramarin, azo-pigments and the like.

Auxilliaries include anti-setting agents, anti-blocking agents, anti-foam agents, anti-flooding agents and the like.

Penetration promoting agents include glycols such as diethylene glycol monobutyl ether, tripropylene glycol monomethyl ether, propyleneglycolmonophenyl ether and the like.

Adhesives include adhesive aid products such as methacrylsilanes, vinylsilanes, titanic acid esters, fatty acid amides, fatty acid amines, and the like.

Emulsifiers include nonylphenol-polyethylene glycol ether, n-alkylphenylsulfonate, oxethylized ricinus oil, and the like.

Water repellants include stearylstearates, calcium or iron stearates, micronized propylene wax, and the like.

As indicated hereinabove, co-biocides may additionally be added to the compositions containing the thiadiazole agents described hereinabove.

The concentrations of active ingredient are in general in the range from 0.05 to 50% by weight and are determined by the requirements of use and the absorptivity of the substrates, i.e., materials. It is more preferred that the active ingredient Formula I is present in amounts ranging from 0.5 to 15% by weight, and more preferably 0.1 to 3% by weight.

For wood preservation, the agents of the present invention are dissolved in carriers such as naphtha fractions or aliphatic or aromatic solvents, such as hexane, toluene or xylene, if necessary with the addition of penetration-promoting agents, binders or other solvents. The active ingredients are used in concentrations of from 0.05 to 5% by weight and are applied in amounts of 50 to 400 g of active ingredient solution per $m^2$ of wood surface, by conventional means, e.g., brushing, injecting and the like.

Very effective wood preservation is achieved if the agents according to the invention, dissolved in suitable substances, are introduced into the wood by special technical methods, for example, the double vacuum process, the vacuum process or the pressure process, so that a load of 0.1 to 3.0—preferably 0.3 to 1.5 kg—of active ingredient of $m^3$ per wood is achieved.

As used herein, the term "agent" or "active ingredient" refers to the thiadiazole compounds of Formula I in combination with the co-biocide, if the latter is present. If the cobiocide is not present, these terms refer to the thiadiazole of Formula I alone.

To preserve woodworking materials, the agents according to the invention—in the form of highly concentrated solutions or formulations containing emulsifiers—can be added to the binder or adhesive in amounts of 0.1 to 2% by weight, based on active ingredients.

To protect textiles, for example, cotton fabrics, from attack by microorganisms, the agents can be dissolved in organic solvents, such as for example in ethanol, xylene or ketones. The active ingredient is preferably present in concentrations of 0.05 to 3% by weight. They can be applied to the textiles by conventional means, such as by means of spraying or impregnation, and, if required, water repellant agents additionally may be added.

The present invention also includes compounds of the present invention is association with cobiocides.

Examples of suitable cobiocides are:

3-iodo-2-propynylbutyl carbamate,
isothiazolones,
copper 8-oxyquinoline,
copper naphthenate,
N,N-dimethyl-N'-phenyl-N'-(fluorodichloromethylthio)-sulfamide,
N-cyclohexyl-N-methoxy-2,5-dimethylfuran-3-carboxamide,
N-propyl-N-2-(2,4,6-trichlorophenoxy)-ethyl-1H-imidazole-carboxamide,
N-trichloromethylphthalimide,
α-[2-(4-chlorophenyl)-ethyl]-α-(1,1-dimethyl)-1H-1,2,4-triazole-1-ethanol,
1-[2-(2,4-dichlorophenyl)-1,3-dioxolan-2-yl]-methyl-1H-1,2,4-triazole,
quaternary ammonium compounds, such as those described hereinabove, tributyltin compounds, such as those described hereinabove and the like.

For the insecticidal treatment too, the agents according to the invention can be combined with corresponding insecticides, such as, for example, permethrin.

As used herein, the term "active ingredient" or "active" agent include the thiadiazoles of the present invention as well as the co-biocides that may be optionally associated therewith.

The compounds of the present invention are prepared by art-recognized techniques. The starting materials re readily available or can easily be prepared by one skilled in the art. The methodology described in DE-A2 142913 are also applicable herein, and the contents thereof are incorporated by reference.

An exemplary example is as follows. A benzamidine of the formula:

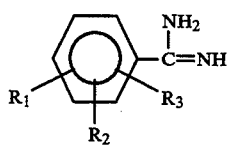

wherein $R_1$, $R_2$ and $R_3$ are as defined herein, and more preferably a salt of benzamides, such as benzamidinum halide is refluxed with a methoxide salt, such as alkali methoxide (e.g. sodium methoxide, potassium methoxide and the like), carbon disulfide and sulfur in methanol to form a thiadiazole compound of the formula:

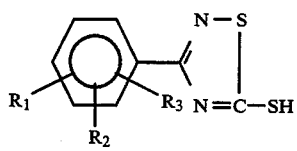

This thiadiazole compound is heated with a base (such as alkali carbonate e.g., potassium carbonate), methylhalide (e.g. methyl iodide) in an inert solvent, such as acetone and the like. The reaction can be effected at room temperature up to the refluxing temperature of the solvent, but it is preferred that the reaction is heated under reflux. It is preferred that the reaction is refluxed for a few hours, preferably 2–3 hours, until the methyl thiadiazole derivative of the formula

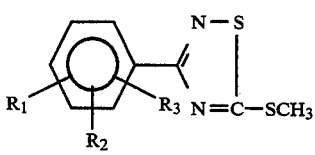

is formed. The product of the reflux is placed into water and the above product of Formula IV is precipitated out. It can be used in the next step without further purification, but it is preferred that the compound of Formula IV is further purified using techniques known to one skilled in the art, such as recrystallization and the like. If recrystallized, it is preformed that is recrystallized from diethyl ether.

The methyl thiadiazole of Formula IV is oxidized with an oxidizing agent, such as hydrogen peroxide, to form the corresponding methyl sulfonyl compound of Formula I.

Naturally, if any of the groups on $R_1$, $R_2$, and $R_3$ are reactive to the reaction conditions described hereinabove, they are protected by protecting groups. These protecting groups re known to one skilled in the art. Examples of such protecting groups are found in Greene, *Protective Groups in Organic Synthesis*, John Wiley & Sons, Inc., New York, 1981, the contents of which are incorporated by reference.

The groups $R_1$, $R_2$ and $R_3$ may be added to the phenyl ring by aromatic substitution reactions known to one skilled in the art. For example, the alkyl group may be added to the aromatic ring by electrophilic alkylation reactions, such as Friedel Crafts alkylation, known to one skilled in the art. The halogen may be added by electrophilic aromatic halogenation, while the nitro group may be added by nitration of the aromatic ring.

The cyano derivative may be formed by nitrating the aromatic ring, reducing the nitro compound with metal or $H_2/Pt$ or $H_2/Pd$, converting the amine to the diazonium ion by reacting the amine with nitrous acid and reacting its diazonium salt with a metal cyanide, such as CuCN under Sandmeyer reaction conditions. All of these techniques are known to one skilled in the art.

The carboxylic acid derivative can be prepared by several techniques known to one skilled in the art, for example, hydrolysis of the nitrile; by formylation or alkylation followed by oxidation; by nucleophilic substitution of the arylhalide with CO, and the like. The esters are prepared from the carboxylic acids; e.g., carboxylic acid is reacted with the alcohol in acid under esterification conditions.

The present invention is further illustrated by the following examples which are not intended to limit the scope thereof.

PREPARATION EXAMPLE:

Synthesis of 5-methylsulfonyl-3-phenyl-1,2,4-thiadiazole 75 g of benzamidinium chloride, 257 g of sodium methylate (30% in methanol), 92 g of carbon disulfide, 19 g of sulfur and 450 g of methanol are refluxed for 6 hours. The excess carbon disulfide is distilled off via a distillation bridge, and the methanol is stripped off in a rotary evaporator. The residue is dissolved in hot water and the solution is filtered. The filtrate is acidified to pH 3 with hydrochloric acid, and the precipitated product is filtered off and taken up in potassium carbonate solution. The solution is filtered and the product is precipitated again with hydrochloric acid.

52 g of the thiadiazole compound 5-thio-3-phenyl-1,2,4-thiadiazole, 18.5 g of potassium carbonate, 54 g of methyl iodide and 270 ml of acetone are refluxed for 3 hours, the mixture is stirred into 1.5 l of water and the white precipitate is then filtered off. The precipitate is recrystallized from diethyl ether.

20 g of 5-methylthio-3-phenyl-1,2,4-thiadiazole are dissolved in 250 ml of acetic acid, and 50 ml of 35% strength hydrogen peroxide solution are added. After 72 hours, the precipitate of 5-methylsulfonyl-3-phenyl-1,2,4-thiadiazole is filtered off and washed with water and hexane.

TESTING OF THE BIOCIDAL ACTION

To test the action, circular paper filters (diameter 2.0 cm for bacteria; diameter 5.5 cm for fungi) were impregnated with the acetone solutions defined in Table 1, and were dried in the air and then placed in Petri dishes on agar which had been inoculated with bacterial suspension or fungus spore suspension and were incubated for 2 days at $+37°$ C. (bacteria) or for 3 weeks at $+30°$ C. (fungi). Thereafter, the inhibitory zones (width of the growth-free zone in mm) around the samples were determined.

Furthermore, a substantial synergistic action was found for mixtures with the thiadiazoles according to the invention with a number of other biocides used for material protection (cf. results in Tables 2 and 3).

TABLE 1

Agar test, inhibitory zones around the samples in mm

5-Methylsulfonyl-3-phenyl-1,2,4-thiadiazole
Impregnating solution in acetone (% by weight)

| | 1.6 | 0.8 | 0.4 | 0.2 | 0 sample |
|---|---|---|---|---|---|
| Bacteria | | | | | |
| Bac. subt. | 20 | 19 | 19 | 15 | 0 |
| Staph. aur. | 22 | 22 | 22 | 20 | 0 |
| Prot. vulg. | 25 | 24 | 24 | 19 | 0 |
| Yeasts | | | | | |
| Cand. alb. | 16 | 16 | 16 | 14 | 0 |
| Fungi | | | | | |
| Asp. niger | 6-8 | 4-5 | 1-2 | 0-1 | 0+++ |
| Trich. vir. | 0-1 | 0 | 0 | 0 | 0+++ |
| Pen. fun. | c.w.g. | c.w.g. | c.w.g. | 12-15 | 0+++ |
| Peac. var. | c.w.g. | c.w.g. | c.w.g. | 10-12 | 0+++ |
| Chaet. glob. | 12-15 | 12-15 | 12-15 | 10-12 | 0+++ |
| Clad. herb. | c.w.g. | c.w.g. | c.w.g. | 12-15 | 0+++ |
| Aureob. pull | c.w.g. | c.w.g. | >15 | 10-12 | 0+++ | c.w.g. = completely without growth
0+++ = Sample completely covered by growth
Bac. subt. = Bacillus subtilis
Staph. aur. = Staphylococcus aureus
Prot. vulg. = Proteus vulgaris
Cand. alb. = Candida albicans
Asp. niger = Aspergillus niger
Trich. vir. = Trichoderma viride
Pen. fun. = Penicillium funicolosum
Peac. var. = Paecilomyces varioti
Chaet. glob. = Chaetomium globosum
Clad. herb. = Cladosporium herbarum
Aureob. pull = Aureobasidium pullulans

TABLE 2a

Agar test, inhibitory zones around the sample in mm

| Impregnating solution | | Fungi | | | |
|---|---|---|---|---|---|
| Biocide | % by weight | Aspergillus niger | Trichoderma viride | Penicillium funicolosum | Paecilomyces varioti |
| MPT* | 0.50 | 5-6 | 0-1 | >15 | c.w.g. |
| MPT | 0.25 | 4-5 | 0 | >15 | >15 |
| A* | 2.0 | 3-4 | 0+ | 0-1 | 1-2 |
| A | 1.0 | 2-3 | 0++ | 0 | 0-1 |
| MPT:A | 0.25:1.0 | 12-15 | 3-4 | c.w.g. | 12-15 |
| MPT:A | 0.125:0.5 | 10-12 | 2-3 | c.w.g. | 10-12 |
| B* | 1.0 | c.w.g. | 0++ | 0++ | 1-2 |
| B | 0.50 | c.w.g. | 0+++ | 0+++ | 0 |
| MPT:B | 0.25:0.5 | c.w.g. | 1-2 | c.w.g. | 6-8 |
| MPT:B | 0.125:0.25 | 12-15 | 0-1 | 10-12 | 1-2 |
| C* | 1.0 | c.w.g. | 12-15 | c.w.g. | 0 |
| C | 0.50 | c.w.g | 10-12 | c.w.g. | 0+ |
| MPT:C | 0.25:0.5 | c.w.g. | 10-12 | c.w.g. | 10-12 |
| MPT:C | 0.125:0.25 | >15 | 3-4 | >15 | 8-10 |
| D* | 1.0 | 3-4 | 2-3 | 12-15 | 6-8 |
| D | 0.50 | 0-1 | 0-1 | 6-8 | 4-5 |
| MPT:D | 0.25:0.5 | 6-8 | 3-4 | c.w.g. | 10-12 |
| MPT:D | 0.125:0.25 | 3-4 | 1-2 | 10-12 | 6-8 |
| 0 samples (without biocide) | | 0+++ | 0+++ | 0+++ | 0+++ |

TABLE 2b

Agar test, inhibitory zones around the samples in mm

| Impregnating solution | | Fungi | | |
|---|---|---|---|---|
| Biocide | % by weight | Chaetomium globosum | Cladosporium herbarum | Aureobasidium pullulans |
| MPT* | 0.50 | 12-15 | 12-15 | c.w.g. |
| MPT | 0.25 | 10-12 | 10-12 | c.w.g. |
| A* | 2.0 | 2-3 | 2-3 | 3-4 |
| A | 1.0 | 1-2 | 1-2 | 2-3 |
| MPT:A | 0.25:1.0 | c.w.g. | 10-12 | c.w.g. |
| MPT:A | 0.125:0.5 | >15 | 6-8 | c.w.g. |
| B* | 1.0 | >15 | 0+ | 3-4 |
| B | 0.50 | >15 | 0++ | 0 |
| MPT:B | 0.25:0.5 | >15 | 8-10 | c.w.g. |
| MPT:B | 0.125:0.25 | 12-15 | 2-3 | c.w.g. |
| C* | 1.0 | c.w.g. | 0+ | c.w.g. |
| C | 0.50 | c.w.g. | 0++ | c.w.g. |
| MPT:C | 0.25:0.5 | c.w.g. | 4-5 | c.w.g. |
| MPT:C | 0.125:0.25 | c.w.g. | 1-2 | c.w.g. |
| D* | 1.0 | 12-15 | 10-12 | 6-8 |
| D | 0.50 | 3-4 | 8-10 | 3-4 |
| MPT:D | 0.25:0.5 | 12-15 | 12-15 | >15 |
| MPT:D | 0.125:0.25 | 6-8 | 6-8 | 5-6 |
| 0 samples (without biocide) | | 0+++ | 0+++ | 0+++ |

MPT* = 5-Methylsulfonyl-3-phenyl-1,2,4-thiadiazole
A* = Tri-n-butyltin naphthenate
B* = 1-[2-(2,4-dichlorophenyl)-1,3-dioxolan-2-yl]methyl-1H-1,2,4-triazole
C* = α-[2-(4-Chlorophenyl)-ethyl]-α-(1,1-dimethyl)-1H-1,2,4-triazole-1-ethanol
D* = Alkyldimethylbenzylammonium chloride
c.w.g. = completely without growth
0+ = no inhibitory zone, slight growth on the sample
0++ = no inhibitory zone, moderate growth on the sample
0+++ = no inhibitory zone, pronounced growth on the sample

TABLE 3

Agar test, inhibitory zones around the samples in mm

| Impregnating solution | | Bacteria | | Yeasts |
|---|---|---|---|---|
| Biocide | % by weight | Bac. subt. | Staph. aur. | Cand. alb. |
| MPT* | 0.5 | 22 | 19 | 20 |
| MPT | 0.25 | 21 | 18 | 18 |
| A* | 2.0 | 7 | 14 | 16 |
| A | 1.0 | 6 | 12 | 16 |
| MPT:A | 0.25:1.0 | 21 | 22 | 21 |
| MPT:A | 0.125:0.5 | 20 | 20 | 20 |
| B* | 1.0 | 0 | 0 | 18 |
| B | 0.5 | 0 | 0 | 17 |
| MPT:B | 0.25:0.5 | 19 | 20 | 20 |
| MPT:B | 0.125:0.2 | 18 | 18 | 20 |
| C* | 1.0 | 9 | 10 | 20 |
| C | 0.5 | 8 | 7 | 18 |
| MPT:C | 0.25:0.5 | 21 | 18 | 30 |
| MPT:C | 0.125:0.25 | 19 | 16 | 25 |
| D* | 1.0 | 18 | 20 | 20 |
| D | 0.5 | 16 | 19 | 14 |
| MPT:D | 0.25:0.5 | 24 | 22 | 21 |
| MPT:D | 0.125:0.25 | 23 | 21 | 18 |
| 0 samples (without biocide) | | 0 | 0 | 0 |

MPT* = 5-Methylsulfonyl-3-phenyl-1,2,4-thiadiazole
A* = Tri-n-butyltin naphthenate
B* = 1-[2-(2,4-dichlorophenyl)-1,3-dioxolan-2-yl]methyl-1H-1,2,4-triazole
C* = α-[2-(4-Chlorophenyl)-ethyl]-α-(1,1-dimethyl)-1H-1,2,4-triazole-1-ethanol
D* = Alkyldimethylbenzylammonium chloride

USE EXAMPLES

Example 1

A colorless formulation containing a small amount of binder and consisting of

| | |
|---|---|
| 1 part by weight of | 5-methylsulfonyl-3-phenyl-1,2,4-thiadiazole |
| 0.1 part by weight of | permethrin |
| 6 parts by weight of | diethylene glycol monobutyl ether |
| 10 parts by weight of | a long-oil alkyd resin (60% strength) |
| 82.9 parts by weight of | high-boiling mineral spirit (crystal oil 60) | exhibits good penetrating power and can be very readily used as a protective wood primer for building timber.

Example 2

A colored protective wood glaze consisting of

| | |
|---|---|
| 1.2 parts by weight of | 5-methylsulfonyl-3-phenyl-1,3,4-thiadiazole |
| 40.0 parts by weight of | a long-oil alkyd resin (50% strength) |
| 0.5 part by weight of | a siccative |
| 0.5 part by weight of | a sedimentation inhibitor |
| 9.2 parts by weight of | iron oxide red paste |
| 0.8 part by weight of | iron oxide black paste |
| 8 parts by weight of | diethylene glycol monobutyl ether |
| 38.8 parts by weight of | high-boiling mineral spirit (crystal oil 60) | is suitable for coating dimensionally stable wood components such as window frames, doors, etc.

Example 3

An active ingredient solution for biocidal treatment of textiles, for example cotton sailcloth, consisting of

| | |
|---|---|
| 2.0 parts by weight of | 5-methylsulfonyl-3-phenyl-1,2,4-thiadiazole |
| 4.4 parts by weight of | micronized polyethylene wax |
| 93.6 parts by weight of | synthetic isoparaffin having little odor | can be applied by spraying the solution or by immersion or impregnation.

Example 4

An active ingredient concentrate consisting of

| | |
|---|---|
| 25 parts by weight of | 5-methylsulfonyl-3-phenyl-1,2,4-thiadiazole |
| 35 parts by weight of | xylene |
| 40 parts by weight of | a nonionic emulsifier | can be used in concentrations of 0.2 to 4 parts by weight for the pot preservation or for the biocidal treatment of aqueous coating systems, for example acrylate-based dispersions.

Example 5

To test the effect of the agents according to the invention in coatings, a commercial plastics emulsion paint (based on an acrylate copolymer) was mixed homogeneously with graded concentrations of the formulation described in Example 4, applied uniformly to PVC sheets (1 mm thick, diameter 5 cm), dried superficially and then placed on biomalt agar in Petri dishes. Samples and agar were sprayed with a fungus spore suspensions, such as *Cladosporum herbarum*, *Aureobasidium pullulans*, *Trichoderma viride*, *Penicillium funicolosum*, *Aspergillus niger* and *Sclerophoma pithyophila*.

The Petri dishes were stored at room temperature and the fungal development on the coatings was evaluated after 3 and 6 weeks.

Samples of coatings without active ingredient and with the commercial product (dithiocarbamate formulation) were also tested as a comparison. The results in Table 3 show the efficacy of the thiadiazole compounds according to the invention.

TABLE 4

| Added active ingredient (% by weight) | Fungal development on emulsion paint coatings after | |
|---|---|---|
| | 3 weeks | 6 weeks |
| Formulation of Example 4 | | |
| 1.0 (= 0.25% of active ingredient) | 1 | 2 |
| 2.0 (= 0.50% of active ingredient) | 0 | 0 |
| 3.0 (= 0.75% of active ingredient) | 0 | 0 |
| Commercial product | | |
| 2.0 | 2 | 4 |
| 4.0 | 2 | 3 |
| 6.0 | 1 | 2 |
| 0 samples (without active ingredient) | 4 | 6 |

0 = Coating completely free of fungal growth
6 = Coating completely covered with fungal growth

Example 6

The effect of the thiadiazole compound according to the invention against wood-destroying fungi was tested by means of a modified "mini-wood-block-test":

Wood blocks of pine sapwood having the dimensions 30×10×5 mm were impregnated with graded concentrations of 5-methylsulfonyl-3-phenyl-1,2,4-thiadiazole in acetone in vacuo, dried in the air, sterilized and exposed to attack by *Gloeophyllum trabeum* in the soil for six weeks. Thereafter, the blocks were dried and the individual weight losses were determined. Wood blocks without active ingredient were simultaneously tested as a control.

The toxicological limits with respect to Basidiomycetes is be determined from the weight losses with respect to different active ingredient concentrations in the wood.

According to the results listed in Table 5, 5-methylsulfonyl-3-phenyl-1,2,4-thiadiazole has a toxic limit of about 0.3–0.5 kg/cm$^3$ of wood with respect to *Gloeophyllum trabeum*.

TABLE 5

| Efficiency test (test fungus: *Gloeophyllum trabeum*) | |
|---|---|
| Concentration of 5-methylsulfonyl-3-phenyl-1,2,4-thiadiazole in the wood (in kg/m$^3$ of wood) | Percentage weight loss (mean values for 3 samples in each case) |
| 0 | 33.4 |
| 0.143 | 30.1 |
| 0.202 | 11.8 |
| 0.291 | 3.9 |
| 0.478 | 1.7 |
| 0.782 | 1.4 |
| 1.08 | 1.5 |

What is claimed is:

1. A wood preservative comprising a wood preserving effective amount of a compound of the formula:

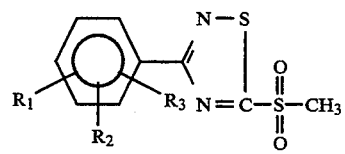

and a wood preservative carrier therefor, wherein
$R_1$, $R_2$ and $R_3$ are independently hydrogen, cyano, halogen, $NO_2$ or COOR, or alkyl having 1–4 carbon atoms which is unsubstituted or substituted with halogen, carboxy, hydroxy or nitro group, or $R_1$, $R_2$ and $R_3$ are alkoxy having 1–4 carbon atoms; and R is hydrogen or lower alkyl.

2. The wood preservative according to claim 1 wherein at least one of $R_1$, $R_2$ and $R_3$ is hydrogen.

3. The wood preservative according to claim 1 wherein at least two of $R_1$, $R_2$ and $R_3$ are hydrogen.

4. The wood preservative according to claim 1 wherein the compound is 5-methylsulfonyl-3-phenyl-1,2,4-thiadiazole.

5. The wood preservative according to claim 1 wherein the compound is present in a concentration ranging from 0.05 to 50% by weight.

6. The wood preservative according to claim 7 wherein the compound is present in concentrations ranging from 0.05 to 5% by weight.

7. The wood preservative according to claim 1 wherein a penetration-promoting agent, emulsifier or binder is additionally present.

8. The wood preservative according to claim 1 wherein a biocide is additionally present.

9. The wood preservative according to claim 8 wherein the biocide is a tributyltin, quaternary ammonium or a triazole.

10. The wood preservative according to claim 8 wherein the biocide is 3-iodo-2-propynylbutyl carbonate, isothiazolone, copper-8-oxyquinoline, copper naphthenate, N,N-dimethyl-N'-phenyl-N'-(fluorodichloromethylthio)sulfamide, N-cyclohexyl-N-methoxy-2,5-dimethylfuran-3-carboxamide, N-propyl-N-2-(2,4,6-trichlorophenoxy)-ethyl-1H-imidazolecarboxamide, N-trichlorormethylphthalimide, α-[2-(4-chlorophenyl)-ethyl]-α-(1,1-dimethyl)-1H-1,2,4-triazole-1-ethanol, or 1-[2-(2,4-dichlorophenyl)-1,3-dioxolan-2-yl]-methyl-1H-1,2,4-triazole.

11. The wood preservative according to claim 9 wherein the tributyltin compound is tri-n-butyltin naphthenate and the quaternary ammonium is alkyl dimethylbenzylammonium wherein the alkyl contains 12–18 carbon atoms.

12. The wood preservative according to claim 8 wherein the ratio of compound to biocide ranges from 1:10 to 10:1 by weight.

13. A method for preserving wood which comprises applying to a surface a wood preservative comprising an effective amount of a thiadiazole of the formula:

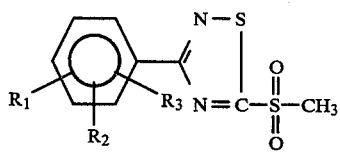

wherein
$R_1$, $R_2$ and $R_3$ are independently hydrogen, cyano, halogen, $NO_2$ or COOR, or alkyl having 1–4 carbon atoms which is unsubstituted or substituted with halogen, carboxy, hydroxy or nitro group, or $R_1$, $R_2$, and $R_3$ are alkoxy having 1–4 carbon atoms; and R is hydrogen or lower alkyl.

14. The method according to claim 13 wherein at least one of $R_1$, $R_2$ and $R_3$ is hydrogen.

15. The method according to claim 13 wherein at least two of $R_1$, $R_2$ and $R_3$ is hydrogen.

16. The method according to claim 13 wherein $R_1$, $R_2$ and $R_3$ is hydrogen.

17. The method according to claim 13 wherein the wood preservative further comprises a carrier.

18. The method of claim 17 wherein the carrier is a liquid carrier.

19. The method according to claim 17 wherein the compound is present in amounts ranging from 0.05 to 5% by weight.

20. The method according to claim 17 wherein the carrier is a liquid carrier, the compound is present in the wood preservative in amounts ranging from 0.05 to 5% by weight and wherein 50 to 400 g of wood preservative is applied per m² of wood surface.

21. The method according to claim 15 wherein 0.1 to 3.0 kg of compound is applied per m³ of wood.

22. The method according to claim 20 wherein 0.3 to 1.5 kg of compound is applied per m³ of wood.

23. The method according to claim 13 wherein the wood preservative further comprises a biocide.

24. The method according to claim 23 wherein the biocide is present in a weight ratio of compound: biocide ranging from 1:10 to 10:1.

25. The method according to claim 22 wherein the biocide contains tributyltin, quaternary ammonium or triazole.

26. The method according to claim 25 wherein the biocide is tri-n-butyltin naphthenate, alkyldimethylbenzyl ammonium halide, wherein the alkyl group contains 12–18 carbon atoms, 3-iodo-2-propynylbutyl carbamate isothiazolones, copper 8-oxyquinoline, copper naphthenate, N,N-dimethyl-N'-phenyl-N'-(fluorodichloromethylthio)sulfamide, N-cyclohexyl-N-methoxy-2,5-dimethylfuran-3-carboxamide, N-propyl-N-2-(2,4,6-trichlorophenoxy)-ethyl-1H-imidazole-carboxamide, N-trichloromethylphthalimide, α-[2-(4-chlorophenyl)-ethyl]-α-(1,1-dimethyl)-1H-1,2,4-triazole-1-ethanol, or 1-[2-(2,4-dichlorophenyl)-1,3-dioxolan-2-yl]-methyl-1H-1,2,4-triazole.

27. A method for protecting substances consisting of textiles, paints, plastics and building materials from microoorganisms which comprises applying to said substances a biocidal effective amount of a compound having a formula:

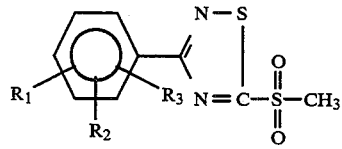

wherein
$R_1$, $R_2$ and $R_3$ are independently hydrogen, cyano, halogen, $NO_2$ or COOR, or alkyl having 1–4 carbon atoms which is unsubstituted or substituted with halogen, carboxy, hydroxy or nitro group, or $R_1$, $R_2$ and $R_3$ are alkoxy having 1–4 carbon atoms; and R is hydrogen or lower alkyl.

28. The method according to claim 27 wherein at least one of $R_1$, $R_2$ and $R_3$ is hydrogen.

29. The method according to claim 27 wherein at least two of $R_1$, $R_2$ and $R_3$ is hydrogen.

30. The method according to claim 27 wherein $R_1$, $R_2$ and $R_3$ is hydrogen.

31. The method according to claim 27 wherein the compound is present with a carrier.

32. The method according to claim 27 wherein the carrier is a liquid carrier.

33. The method according to claim 31 wherein the compound is present in amounts ranging from 0.05% to 50% by weight.

34. The method according to claim 33 wherein the compound is present in amounts ranging from 0.05 to 15% by weight.

35. The method according to claim 34 wherein the compound is present in amounts ranging from 0.05 to 3% by weight.

36. The method according to claim 35 wherein the compound is present in amounts ranging from 0.1 to 3% by weight.

37. The method according to claim 26 wherein a biocide is additionally present with said compound.

38. The method according to claim 37 wherein the biocide is present in a weight ratio of compound: biocide ranging from 1:10 to 10:1.

39. The method according to claim 37 wherein the biocide contains tributyltin, quaternary ammonium or triazole.

40. The method according to claim 37 wherein the biocide is tri-n-butyltin napthtenate, alkyldimethylbenzyl ammonium halide wherein the alkyl groups contain 12–18 carbon atoms, 3-iodo-2-propynylbutyl carbamate isothiazolones, copper 8-oxyquinoline, copper nephthenate, N,N-dimethyl-N'-phenyl-N'-(fluorodichloromethylthio)sulfamide, N-cyclohexyl-N-methoxy-2,5-dimethylfuran-3-carboxamide, N-propyl-N-2-(2,4,6-trichlorophenoxy)-ethyl-1H-imidazole-carboxamide N-trichloromethylphthalimide, α-[2-(4-chlorophenyl)-ethyl]-α-(1,1-dimethyl)-1H-1,2,4-triazole-1-ethanol, or 1-[2-(2,4-dichlorophenyl)-1,3-dioxolan-2-yl]-methyl-1H-1,2,4-triazole.

* * * * *

UNITED STATES PATENT AND TRADEMARK OFFICE
CERTIFICATE OF CORRECTION

PATENT NO. : 5,344,482
DATED : September 6, 1994
INVENTOR(S) : Horst Landsiedel, et al.

It is certified that error appears in the above-indentified patent and that said Letters Patent is hereby corrected as shown below:

In the Abstract, line 22: "to-the" should read --to the--

Column 1, line 22: delete "Formula 6" and insert --I--

Signed and Sealed this

Twenty-seventh Day of December, 1994

Attest:

BRUCE LEHMAN

*Attesting Officer*   *Commissioner of Patents and Trademarks*